United States Patent [19]
Tennican et al.

[11] Patent Number: 5,308,322
[45] Date of Patent: May 3, 1994

[54] CENTRAL VENOUS CATHETER ACCESS SYSTEM

[76] Inventors: Patrick O. Tennican, W. 105 8th Ave., Suite 350, Spokane, Wash. 99204; L. Myles Phipps, 2811 E. 11th, Spokane, Wash. 99202; Russell A. Michaelsen, P.O. Box 847, Spokane, Wash. 99210

[21] Appl. No.: 48,906

[22] Filed: Apr. 19, 1993

[51] Int. Cl.$^5$ ............................................. A61M 37/00
[52] U.S. Cl. .................................... 604/83; 604/183
[58] Field of Search ............ 604/83, 87, 88, 183–185, 604/212, 216

[56] References Cited

U.S. PATENT DOCUMENTS

| | | | |
|---|---|---|---|
| 2,117,469 | 5/1938 | Woodyatt | 128/215 |
| 2,876,770 | 7/1959 | White | 604/232 |
| 2,950,717 | 7/1960 | Bouet | 604/216 |
| 3,270,743 | 9/1966 | Gingras | 604/192 |
| 3,340,869 | 9/1967 | Bane | 604/216 |
| 3,411,503 | 11/1968 | Santomieri | 128/216 |
| 3,473,524 | 10/1969 | Drewe | 128/6 |
| 3,712,295 | 1/1973 | Kline | 128/2 F |
| 3,796,542 | 3/1974 | Kline | 23/230 B |
| 3,911,916 | 10/1975 | Stevens | 128/218 R |
| 3,923,058 | 12/1975 | Weingarten | 128/218 R |
| 3,933,439 | 1/1976 | McDonald | 23/259 |
| 3,938,514 | 7/1976 | Boucher | 128/235 |
| 4,055,177 | 10/1977 | Cohen | 128/218 |
| 4,187,861 | 7/1980 | Heffernan | 128/764 |
| 4,243,035 | 1/1981 | Barrett | 128/215 |
| 4,245,655 | 1/1981 | Patel | 128/765 |
| 4,335,717 | 6/1982 | Bujan et al. | 128/214 G |
| 4,411,656 | 10/1983 | Cornett, III | 128/212 |
| 4,424,057 | 1/1984 | House | 604/88 |
| 4,453,934 | 6/1984 | Gahwiler et al. | 604/191 |
| 4,501,582 | 2/1985 | Schulz | 604/52 |
| 4,509,109 | 11/1985 | Tischlinger | 128/218 M |
| 4,643,721 | 2/1987 | Brunet | 604/191 |

(List continued on next page.)

FOREIGN PATENT DOCUMENTS

| | | | |
|---|---|---|---|
| 8701944 | 4/1987 | PCT Int'l Appl. | 604/212 |
| WO92/11044 | 7/1992 | PCT Int'l Appl. | |

OTHER PUBLICATIONS

Lyo-Ject II Dual-Chamber, Prefilled Syringe, *Journal of Intravenous Nursing*, vol. 13, No. 4, p. 261.
TUBEX Blunt Pointe, advertisement.
SAFSITE System, advertisement.
Auto-SASH IV Site Flushing System, advertisement.

*Primary Examiner*—Jerome L. Kruter
*Attorney, Agent, or Firm*—Wells, St. John, Roberts, Gregory & Matkin

[57] ABSTRACT

A central venous catheter (CVC) access system includes a manifold barrel which is connectable to an access lumen of a central venous catheter. Integrated flush and reagent syringes are connected in fluid communication with the manifold barrel. A fluid withdrawal syringe and a transfer lumen are also connected in fluid communication with the manifold barrel. The fluid withdrawal syringe allows withdrawal of waste blood and anti-coagulant from the CVC. The transfer lumen allows injection and withdrawal of fluids through the CVC access lumen. The flush syringe is initially pre-filled with saline which at the appropriate time is injected into the manifold barrel to flush administered medication into the patient's blood stream. The reagent syringe is initially pre-filled with a blood anti-coagulant for injection into the CVC at the conclusion of the CVC access procedure. A multi-stage injection syringe is also disclosed for sequentially injecting at least two fluids into the manifold barrel. In addition, an improved blood collection device is described for use with the CVC access system. The blood collection device includes a rigid cylindrical syringe tube and a rubber or rubber-like plunger which is slidably received therein. Instead of a conventional plunger handle, however, a tension line extends rearwardly from the plunger. The tension line is operable to pull or withdraw the plunger rearwardly, but is inoperable to push the plunger back toward the forward end of the syringe once it has been withdrawn.

18 Claims, 7 Drawing Sheets

U.S. PATENT DOCUMENTS

| | | | |
|---|---|---|---|
| 4,666,429 | 5/1987 | Stone | 604/83 |
| 4,693,706 | 9/1987 | Ennis, III | 604/87 |
| 4,715,854 | 12/1987 | Vaillancourt | 604/191 |
| 4,725,267 | 2/1988 | Vaillancourt | 604/192 |
| 4,753,638 | 6/1988 | Peters | 604/212 |
| 4,775,369 | 10/1988 | Schwartz | 604/253 |
| 4,790,828 | 12/1988 | Dombrowski et al. | 604/198 |
| 4,795,432 | 1/1989 | Karczmer | 604/110 |
| 4,795,441 | 1/1989 | Bhatt | 604/124 |
| 4,799,926 | 1/1989 | Haber | 604/187 |
| 4,804,371 | 7/1989 | Vaillancourt | 604/198 |
| 4,850,977 | 7/1989 | Bayless | 604/198 |
| 4,863,434 | 9/1989 | Bayless | 604/198 |
| 4,863,435 | 9/1989 | Sturman et al. | 604/198 |
| 4,887,998 | 12/1989 | Martin et al. | 604/110 |
| 4,894,055 | 1/1990 | Sudnak | 604/198 |
| 4,915,688 | 4/1990 | Bischof et al. | 604/83 |
| 4,921,490 | 5/1990 | Spier et al. | 604/192 |
| 4,927,416 | 5/1990 | Tomkiel | 604/198 |
| 4,929,241 | 5/1990 | Kulli | 604/263 |
| 4,935,013 | 6/1990 | Haber et al. | 604/192 |
| 4,950,250 | 4/1990 | Haber et al. | 604/192 |
| 4,966,592 | 10/1990 | Burns et al. | 604/198 |
| 4,978,344 | 12/1990 | Dombrowski et al. | 604/198 |
| 5,030,210 | 7/1991 | Alchas | 604/247 |
| 5,037,390 | 8/1991 | Raines et al. | 604/88 |
| 5,046,508 | 9/1991 | Weissler | 128/763 |
| 5,053,017 | 10/1991 | Chamuel | 604/192 |
| 5,059,180 | 10/1991 | McLees | 604/110 |
| 5,092,851 | 3/1992 | Ragner | 604/192 |
| 5,102,388 | 3/1992 | Richmond | 604/88 |
| 5,108,379 | 4/1992 | Dolgin et al. | 604/198 |
| 5,140,996 | 8/1992 | Sommers et al. | 128/849 |
| 5,192,274 | 3/1993 | Bierman | 604/180 |

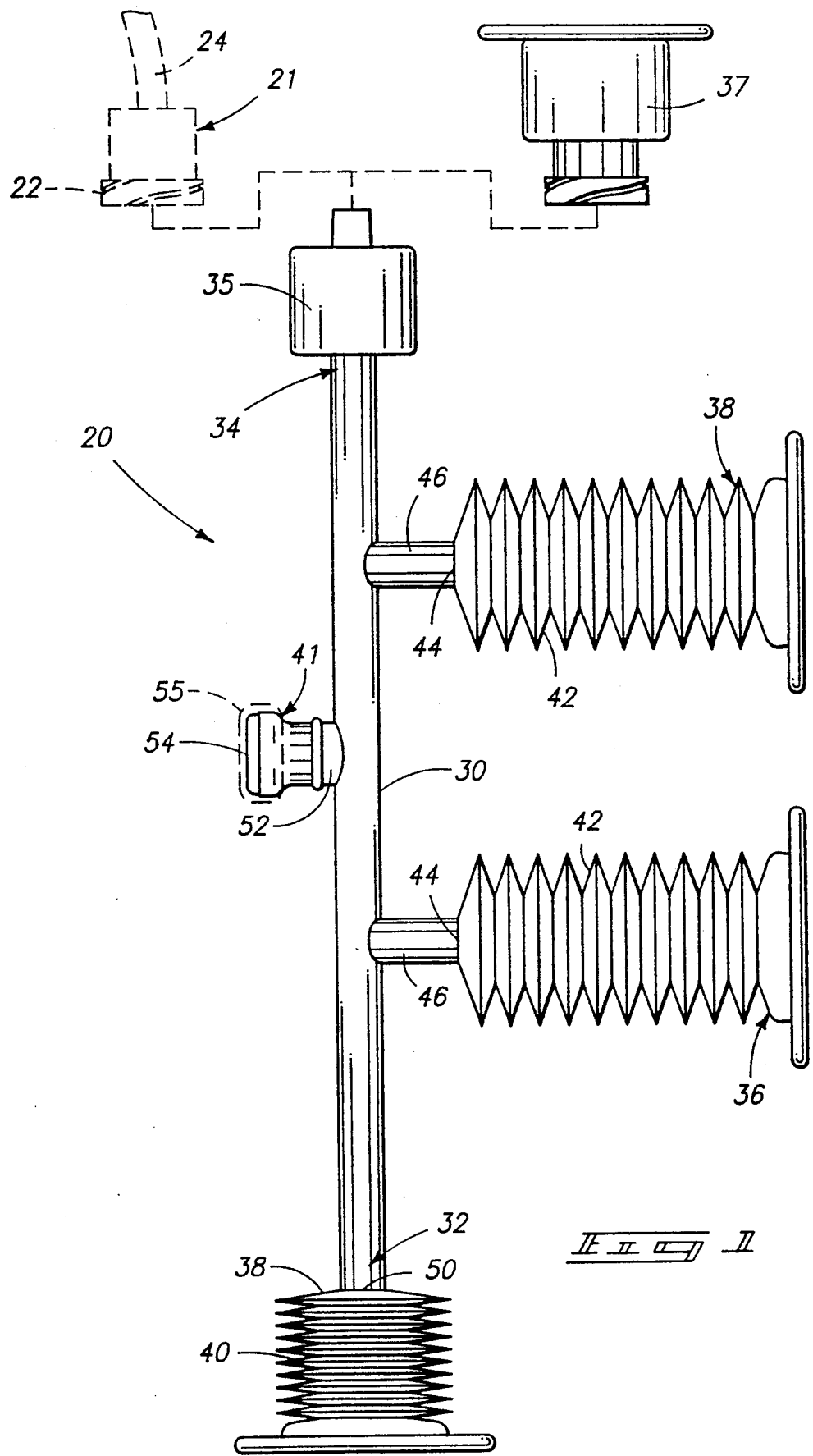

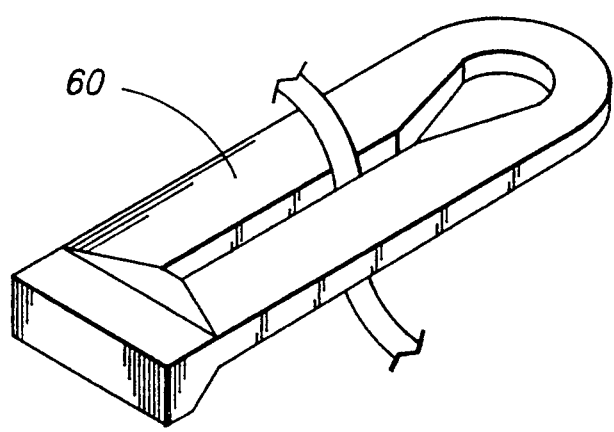

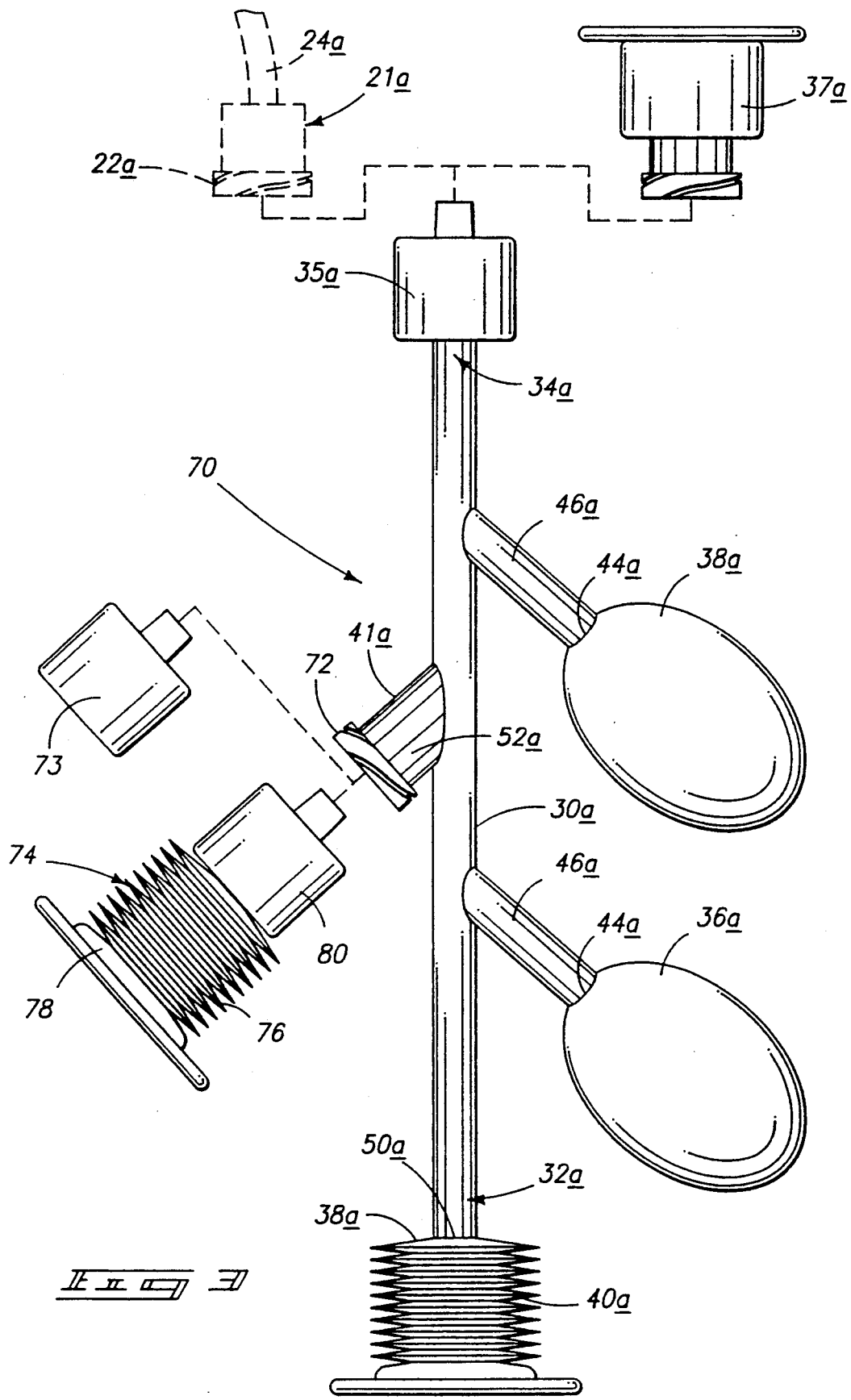

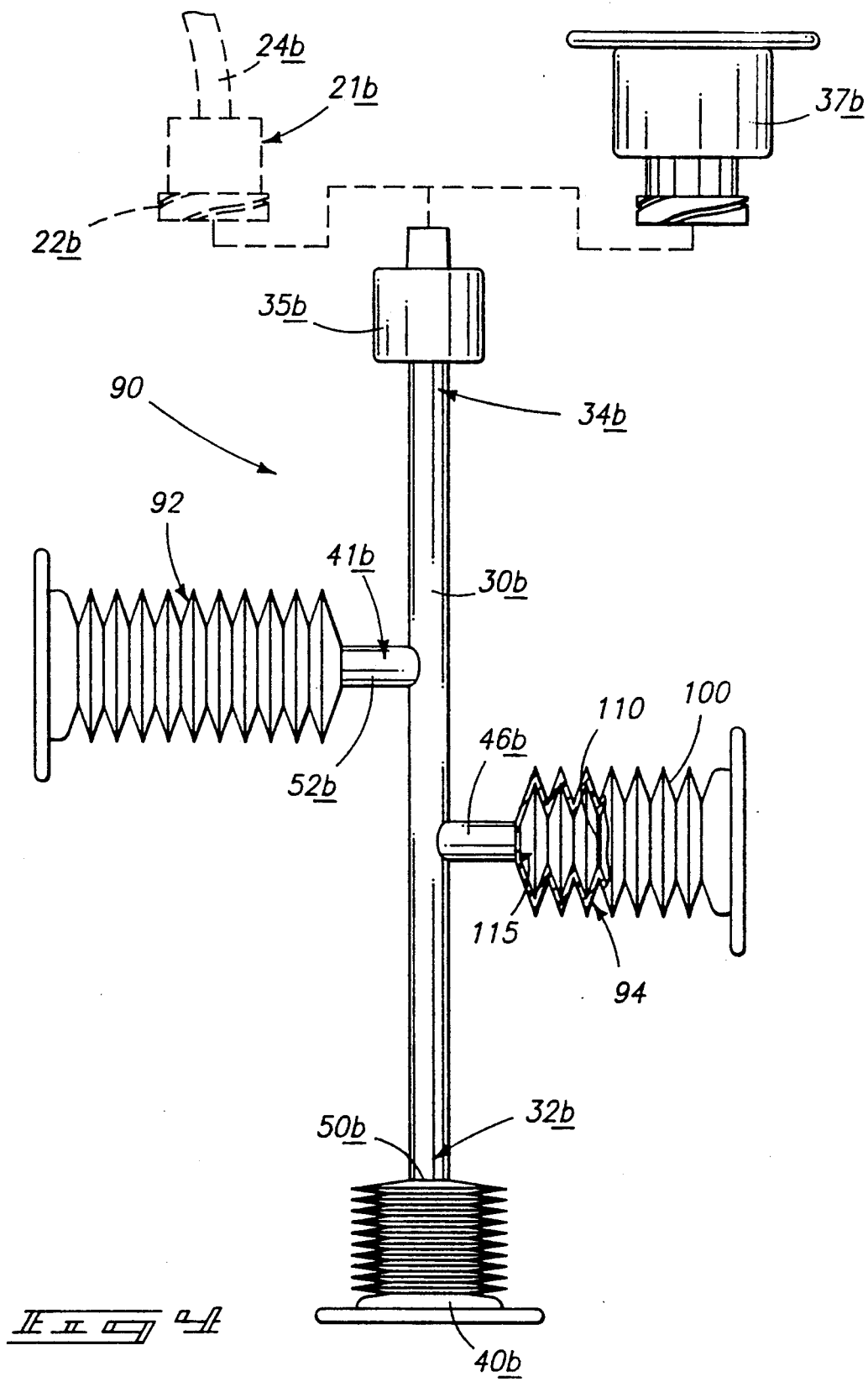

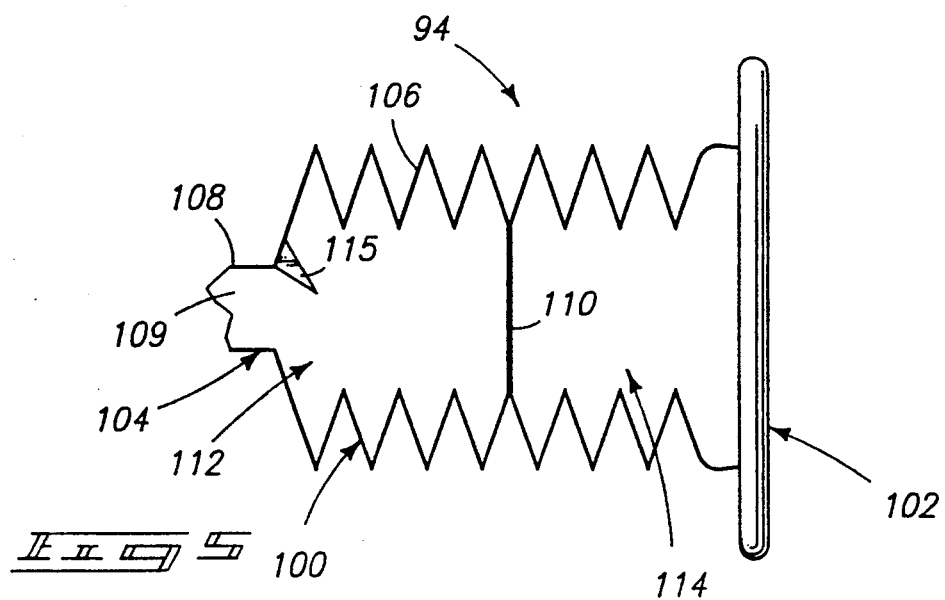
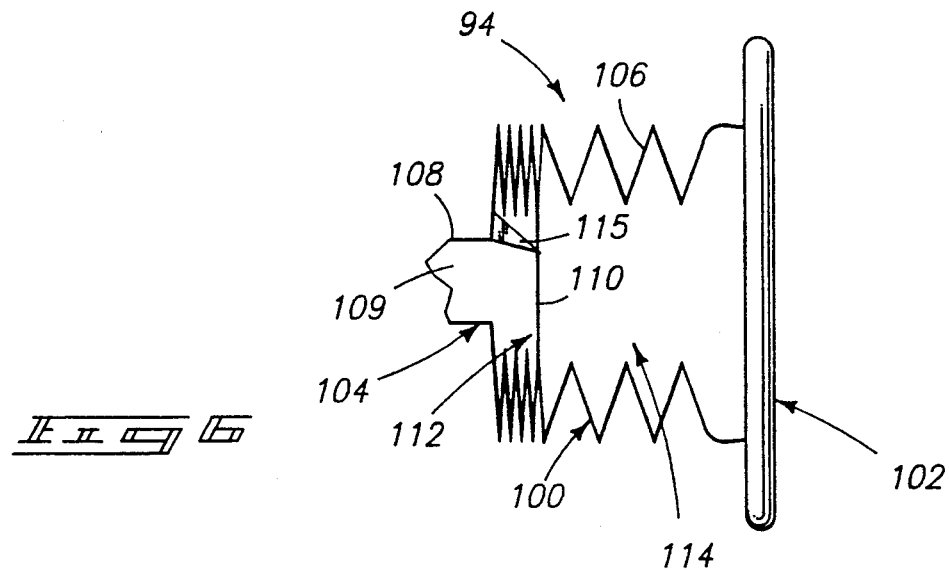
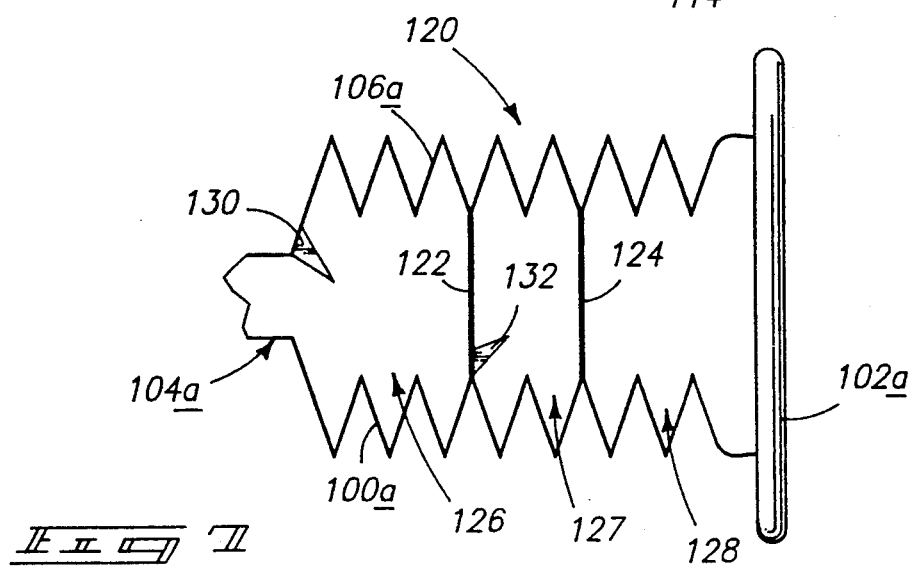

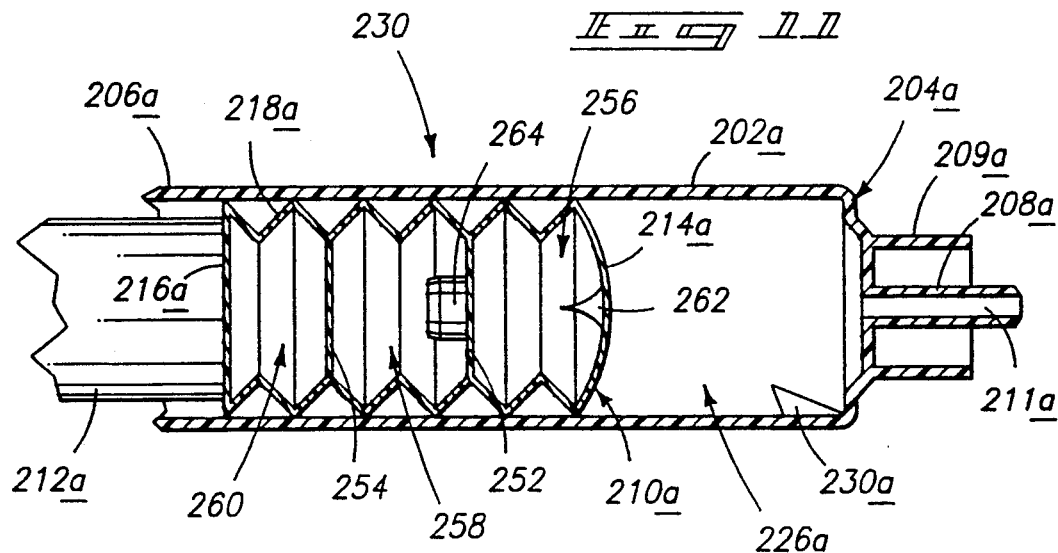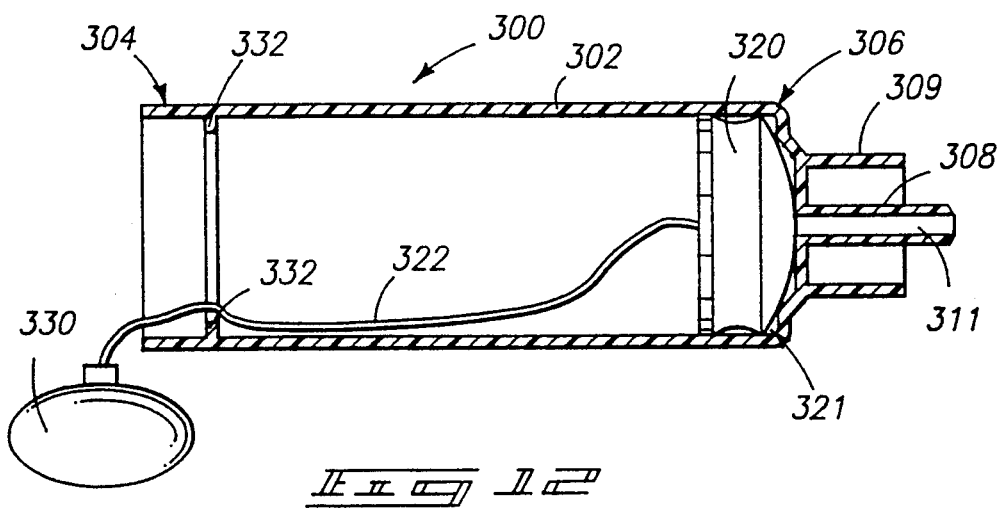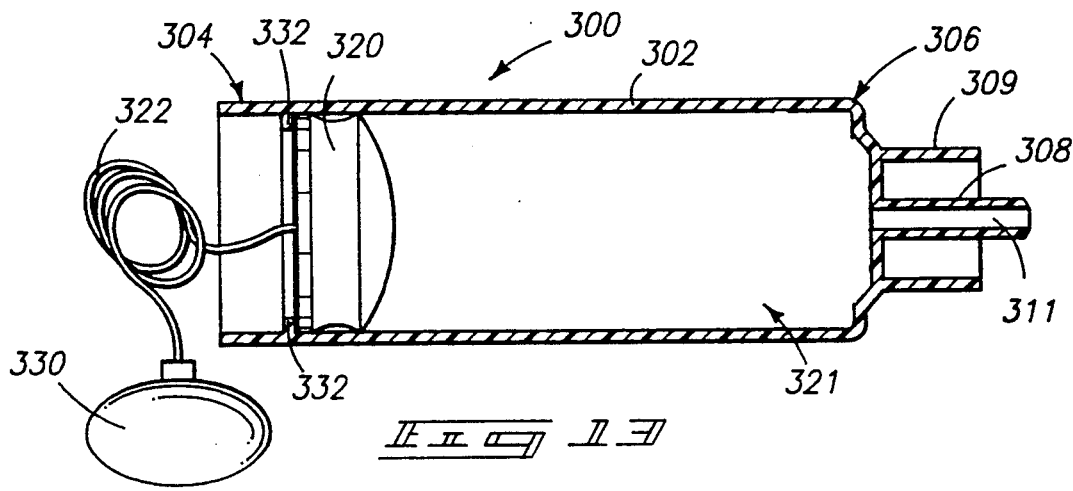

CENTRAL VENOUS CATHETER ACCESS SYSTEM

TECHNICAL FIELD

This invention relates to central venous catheter access operations and devices, and to syringes.

BACKGROUND OF THE INVENTION

A central venous catheter (CVC) is an intravenous access into the central, large-vein portion of a person's blood stream. A CVC provides a way of injecting medication or sampling blood very near to the person's heart. A CVC thus includes an access lumen to which is connected an injection port in the form of a pierceable rubber membrane. Fluid transfer through the CVC requires first cleaning the pierceable membrane with alcohol and/or Betadine and then inserting a hypodermic syringe needle through the membrane. This provides direct access to the patient's blood stream.

The pierceable membrane is often provided as part of a removable injection port. Conventional luer-lock connectors allow removable mating or hook-up between the CVC and the injection port. Thus, an alternative method of accessing the CVC is to remove the injection port and attach a syringe tip directly to the CVC access lumen.

The main purpose of a CVC is to allow fluid injection and withdrawal to and from a patient's blood stream. A CVC is placed in a patient by surgical procedure, and is attached to the skin by sutures. A CVC is often left in place for a relatively long time. The skin entry point is kept covered by a carefully monitored dressing. Because of the direct nature of access into a patient's blood stream, infection control when dealing with CVCs is of utmost importance. In most institutions, only registered nurses and doctors are allowed to perform procedures relating to CVC access.

CVC access lumens can become clogged by clotted blood. Accordingly, such lumens are kept open by injecting a Heparin solution into them. Heparin is a protein material which acts as a blood anti-coagulant to interfere with blood clotting. Before transferring fluid to or from a patient through the CVC, it is sometimes desired or necessary to remove this Heparin and the blood containing such Heparin.

There are significant risks associated with transferring fluid through a CVC. One risk is that of microbial infection. Another significant risk is that of air embolism. Both of these risks are potentially life-threatening and increase significantly with each hook-up through the CVC access lumen, especially when such a hook-up is by way of a needle and pierceable membrane. Compounding these risks is the fact that a single medication injection procedure or a single blood collection procedure can require four or more hook-ups to the CVC access lumen, one for each separate fluid injection and withdrawal through the CVC access lumen. In some cases, the CVC is used for medication injection or blood withdrawal as many as four to six times each day. Thus, as many as 24 hook-ups are required every day, with a corresponding number of opportunities for infection or air embolism. Over the period of a month, the CVC could present over 700 opportunities for life-threatening events to occur.

As an example, a simple medication injection procedure requires the following steps. First, the pierceable membrane of the injection port must be cleaned with alcohol. The success of this step is highly dependent on the skill of the care-giver and is subject to mistakes caused by carelessness or inattentiveness. A waste blood withdrawal device such as a hypodermic syringe is subsequently prepared and its needle inserted through the membrane. The syringe is operated to withdraw Heparin-containing blood from the CVC. A medication syringe is then prepared, its needle inserted through the pierceable membrane, and medication injected into the CVC. Subsequently, a "flush" syringe is prepared with sterile saline solution. The sterile saline is injected through the pierceable membrane into the CVC to carry the medication into the patient's blood stream. Finally, a Heparin syringe is prepared and Heparin is injected into the CVC through the pierceable membrane to prevent clotting.

Withdrawing or collecting blood requires similar steps. First, Heparin or Heparin-containing blood is withdrawn from the CVC transfer lumen by injecting a needle through the pierceable membrane and withdrawing blood into a syringe. A blood withdrawal syringe or other blood collection device is then prepared and its needle inserted through the CVC pierceable membrane. After a sufficient amount of blood is withdrawn, the blood withdrawal syringe is removed. First a normal saline flush of 20 milliliters is injected, then a Heparin syringe is prepared and its needle inserted through the pierceable membrane. A prescribed amount and concentration of Heparin is injected into the transfer lumen to prevent subsequent blood clotting.

As is apparent from the above discussion, another problem with standard CVC access procedures is that the various solutions and syringes needed to access a CVC are supplied separately. Often, a nurse must track down each piece of equipment separately. This can be a costly and time consuming process. Furthermore, even after proper equipment is found, such equipment is often not designed to work together as a system.

Because of this, CVC procedures often require more than one person. Since CVC operations are performed only by registered nurses or doctors, the time expended by these persons is relatively valuable. In addition, other personnel are often forced to remain idle while waiting for the qualified persons to find time to provide the service.

As an additional complication, access to a CVC by needle gives rise to a potential source of injury and infection to the care giver through contact with the needle. This is particularly important when the patient being treated has a dangerous infection, such as HIV or Hepatitis. Often, even the care giver is unaware that the patient has such as infection.

Blood withdrawal through a CVC involves additional problems. A blood collection device is often in the form of a conventional plunger-type syringe. However, subsequent processing of blood cannot take place in such a syringe. Accordingly, it is necessary to transfer blood from such a blood collection syringe to a suitable container for centrifugal processing or other treatment. Furthermore, it is often desirable to have a reagent such as an anti-coagulant within the blood collection device prior to blood collection.

A "Vacutainer blood withdrawal tube" is often used to alleviate the blood collection problems noted above. A Vacutainer blood withdrawal tube is an evacuated tube which is suitable for use in subsequent blood processing steps. It has a forward end which can be connected to a hypodermic needle or mating connector which is in turn connected to a source of blood. Once connected, the vacuum within the Vacutainer blood withdrawal tube draws blood into the container. However, Vacutainer blood withdrawal tube have their own problems. For instance, it is impossible when using a Vacutainer blood withdrawal tube to regulate the amount of withdrawing pressure imparted to a patient's blood stream. The initial vacuum is usually quite high, and is applied very suddenly. Thus, collapse of or damage to veins often results from the initial connection of the Vacutainer blood withdrawal tube to a vein or blood vessel.

The invention described below reduces the number of sequential connections which are required to administer medication or to withdraw blood through a CVC. In addition, several embodiments of the invention completely eliminate hypodermic needles from the process. Furthermore, an improved blood collection device is disclosed for connection to the CVC access system. The improved blood collection device eliminates the problems noted above and exhibits additional desirable characteristics which will become apparent. Furthermore, the CVC access system described below is conveniently supplied together as an integrated system, thus reducing much of the work previously associated with CVC operations and procedures.

BRIEF DESCRIPTION OF THE DRAWINGS

Preferred embodiments of the invention are described below with reference to the accompanying drawings:

FIG. 1 is a front view of a CVC access system in accordance with a first preferred embodiment of the invention;

FIG. 2 is a perspective view of a tubing clamp in accordance with a preferred embodiment of the invention;

FIG. 3 is a front view of a CVC access system in accordance with a second preferred embodiment of the invention;

FIG. 4 is a front view of a CVC access system in accordance with a third preferred embodiment of the invention;

FIG. 5 is a diagrammatic view of a multi-phase injection syringe in accordance with one preferred embodiment of the invention;

FIG. 6 is a diagrammatic view of the multi-phase injection syringe of FIG. 5, the syringe being shown in a partially compressed condition;

FIG. 7 is a diagrammatic view of a multi-phase injection syringe in accordance with another preferred embodiment of the invention;

FIG. 11 is a sectional front view of a multi-phase injection syringe in accordance with yet another embodiment of the invention;

FIG. 12 is a sectional front view of a blood collection device in accordance with a preferred embodiment of the invention; and FIG. 13 is a sectional front view of the blood collection device of FIG. 12, the blood collection device being shown with its plunger withdrawn.

DETAILED DESCRIPTION OF THE PREFERRED EMBODIMENTS

Figure 8:
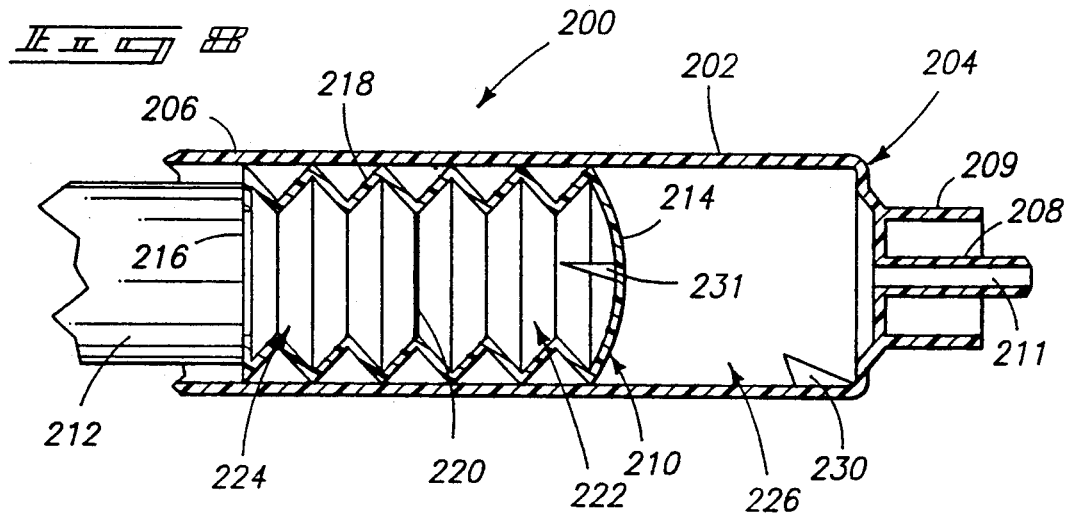
FIG. 8 is a sectional front view of a multi-phase injection syringe in accordance with yet another embodiment of the invention.

This disclosure of the invention is submitted in furtherance of the constitutional purposes of the U.S. Patent Laws "to promote the progress of science and useful arts." U.S. Constitution, Article 1, Section 8.

In accordance with one aspect of the invention, a central venous catheter access system comprises:

a manifold barrel having a forward end which is connectable to a central venous catheter;

a flush syringe connected in fluid communication with the manifold barrel;

a fluid withdrawal syringe connected in fluid communication with the manifold barrel; and a transfer lumen connected in fluid communication with the manifold barrel, the transfer lumen allowing fluid passage between a transfer syringe and the manifold barrel.

In accordance with another aspect of the invention, a multi-phase syringe for sequentially injecting multiple fluids comprises:

a collapsible hollow body;

a syringe tip having an opening through which fluid passes from the hollow body first cell upon compression of the collapsible hollow body; and a septum within the hollow body, the septum dividing the body into first and second cells, the septum being breachable to allow fluid passage from the second cell of the hollow body through the syringe tip opening after the first cell of the hollow body has been at least partially emptied by partial compression of the hollow body.

In accordance with yet another aspect of the invention, a blood collection tube comprises:

a rigid syringe tube extending from a rearward end to a forward end, the rigid tube having a hollow interior;

a syringe tip formed in the forward end of the syringe tube;

a plunger which is slidably received within the hollow interior of the syringe tube, the plunger defining a variable blood collection volume in the forward end of the syringe tube; and a tension line connected to the plunger and extending rearward from the plunger through the rearward end of the syringe tube, the tension line being operable to pull the plunger toward the rearward end of the syringe tube to increase the blood collection volume and to draw blood into the syringe tube, the tension line being inoperable to push the plunger back toward the forward end of the syringe tube.

FIG. 1 shows a first embodiment of a central venous catheter (CVC) access system in accordance with the invention, generally designated by the reference numeral 20. CVC access system 20 is designed for removable connection to an injection or access lumen of a conventional CVC. Such an access lumen 21 is shown in FIG. 1 as a standard female luer-lock connector 22 extending from a CVC tube 24. Luer-lock connector 22 would typically be capped when not in use.

CVC access system 20 generally comprises a disposable manifold barrel 30 with multiple access ports for sequentially injecting and withdrawing fluids from a CVC. In the preferred embodiments, a plurality of injection or withdrawal syringes are provided integrally with a manifold barrel. The injection syringes, withdrawal syringes, and manifold itself are pre-filled with appropriate fluids so that everything or nearly everything needed for a CVC access operation is included in one disposable package. Such pre-filling also reduces risks of air embolism. A new luer-lock medication port is also provided in the package to recap the CVC after use.

Manifold barrel 30 extends from a rearward end 32 to a forward end 34. Barrel 30 is typically formed of a material similar to conventional medically-approved tubing, but could alternatively be fabricated from a number of plastic or plastic-like materials such as those typically used in medical applications. A somewhat flexible material is advantageous in many respects to allow convenient alignment and placement of the CVC access system relative to a patient. It also allows the system to be easily clamped at appropriate locations to isolate sections of the system from each other.

Forward end 34 of manifold barrel 30 is provided with a male luer-lock connector 35 for connection to female luer-lock connector 22 of CVC access lumen 21. A removable cap 37 is provided for mating with luer-lock connector 35 until the system is used.

At least two injection syringes are associated with a manifold barrel 30: a flush injection syringe 36 and a reagent injection syringe 38. Each of these injection syringes is connected to manifold barrel 30 between its rearward and forward ends 32 and 34. In addition, a fluid or waste blood withdrawal syringe 40 is associated with manifold barrel 30, as is a fluid transfer lumen 41. Each of the syringes and the transfer lumen are connected in fluid communication with manifold barrel 30 to allow sequential injection and withdrawal of fluids while requiring only a single hook-up or connection to CVC access lumen 21.

Injection syringes 36 and 38 can take many forms, although they are preferably provided integrally with manifold barrel 30. In the preferred embodiment shown by FIG. 1, syringes 36 and 38 comprise syringe tubes which are molded of a flexible material, having sidewalls 42 in the form of accordion-like bellows or folds. The syringe tubes are hollow, defining an interior fluid volume. The accordion-like folds allow axial compression of the injection syringes to decrease their interior fluid volume. Each of syringes 36 and 38 has a forward opening 44 which allows fluid passage into manifold barrel 30. Short lengths 46 of flexible tubing extend between forward openings 44 and manifold barrel 30, at right angles to manifold barrel 30, to allow fluid communication between the syringes and the manifold barrel. Tubing lengths 46 are preferably clamped to isolate the injection syringes from manifold barrel 30. Suitable clamps 60, such as shown in FIG. 2, are used for this purpose. Other clamps might be substituted for the particular clamps shown, such as clamps which are formed integrally with the various tubes. Alternatively, inline valves can be appropriately positioned to selectively isolate the various portions of the system from each other. Such valves might be in the form of rotary valves or pinch-type valves.

Syringes 36 and 38 are pre-filled with appropriate fluids. As noted above, the syringes are compressible to selectively inject their fluids into manifold barrel 30 and CVC access lumen 21. Flush syringe 36 is typically pre-filled with a flush fluid, such as normal saline solution. Reagent syringe 38 is typically filled with a reagent fluid such as a blood anti-coagulant for selective injection into manifold barrel 30. Heparin is an example of such a blood anti-coagulant. Reagent syringe 38 is connected to manifold barrel 30 forward of where flush syringe 36 is connected.

Fluid withdrawal syringe 40 is connected at the manifold barrel rearward end 32 in fluid communication with manifold barrel 30. It is preferably provided integrally with manifold barrel 30. As is the case with injection syringes 36 and 38, fluid withdrawal syringe 40 can take many forms. In the preferred embodiment shown, however, fluid withdrawal syringe 40 is constructed in a manner similar to injection syringes 36 and 38, comprising a syringe tube with sidewalls in the form of accordion-like bellows or folds. The syringe tube is hollow, defining an interior fluid volume. Fluid withdrawal syringe 40, as provided with manifold barrel 30, is initially in a compressed or collapsed form. However, the accordion-like folds allow axial expansion of the withdrawal syringe to increase its interior fluid volume and to withdraw fluid from CVC access lumen 21 into manifold barrel 30. Withdrawal syringe 40 has a forward opening 50 which is connected directly to rearward end 32 of manifold barrel 30 for fluid communication therewith. Rearward end 32 of manifold barrel 30 is selectively clamped off or isolated from manifold barrel 30 by a clamp 60 such as shown in FIG. 2.

Transfer lumen 41 is connected for fluid communication with manifold barrel 30 between fluid withdrawal syringe 40 and manifold barrel forward end 34. More specifically, it is connected to manifold barrel 30 forward of both withdrawal syringe 40 and flush syringe 36, but rearward of reagent syringe 38. Transfer lumen 41 comprises a short tube 52 which extends at a right angle from manifold barrel 30. The transfer lumen includes fluid connection means for allowing fluid connection and passage between a transfer syringe (not shown). The connection means more specifically comprises a pierceable rubber or rubber-like membrane 54 positioned relative to the transfer lumen to allow a transfer syringe needle to be inserted into transfer lumen 41.

CVC system 20 can be used either to inject medication or other solutions into a patient through a CVC, or to withdraw a patient's blood through the CVC. In either case, the sequence of steps required to accomplish fluid transfer to or from the patient can be accomplished without the numerous devices and sequential connections previously required.

As an example, typical steps involved in administering a patient medication are described below. CVC access system 20 is provided in a pre-filled condition, ready for immediate connection to CVC access lumen 21. Flush syringe 36 is pre-filled with saline. Reagent syringe 38 is pre-filled with a blood anti-cogulant such as Heparin. Withdrawal syringe 40, used for waste blood withdrawal, initially contains a small volume of saline. Also, the internal volume of manifold barrel 30 itself is initially pre-filled with saline. Flush syringe 36, reagent syringe 38, and withdrawal syringe 40 are initially clamped off from manifold barrel 30 with clamps 60 to prevent fluid transfer from the syringes into manifold barrel 30.

The various components described above form an internal system volume which is pre-filled with liquid to substantially eliminate air from the internal system volume. Because all internal portions of CVC access sysem 20 are pre-filled with liquid, the risk of air embolism is greatly reduced by using CVC access system 20 rather than conventional methods.

Connecting CVC access system 20 to CVC access lumen 21 prior to medication injection requires first clamping CVC tube 24 and removing any cap installed over CVC female luer-lock connector 22. Forward end 34 of manifold barrel 30 is also clamped and cap 37 is removed. Female and male luer-lock connectors 22 and 35 are subsequently mated, and the clamps removed from CVC tube 24 and manifold barrel 30. Fluid present within the connector passages prevents air entry.

To remove Heparin from CVC access lumen 21 prior to medication injection, collapsed withdrawal syringe 40 is unclamped from manifold barrel 30 to allow fluid communication therebetween. Withdrawal syringe 40 is then expanded to withdraw Heparin-containing blood rearward into manifold barrel 30, past injection syringes 36 and 38, and into withdrawal syringe 40. Withdrawal syringe 40 is subsequently clamped off from manifold barrel 30. In some cases, particularly where very low concentrations of Heparin are used, the waste blood withdrawal step may be omitted.

Flush syringe 36 is then unclamped from manifold barrel 30 to allow fluid communication therebetween. Flush syringe 36 is compressed to inject saline into manifold 30 and CVC access lumen 21 in a first amount according to protocol. Flush syringe 36 is subsequently clamped off from manifold barrel 30.

A transfer syringe (not shown) is prepared with the desired medication, and its needle (not shown) is inserted through membrane 54 into transfer lumen 41. The medication is then injected into manifold 30 through transfer lumen 41.

At this point, flush syringe 36 is again unclamped from manifold barrel 30 to allow fluid communication therebetween, and compressed to inject saline into manifold 30 and through CVC access lumen 21 into a patient in a second amount according to protocol. Flush syringe 36 is subsequently clamped off from manifold barrel 30.

Reagent syringe 38 is then unclamped from manifold barrel 30 to allow fluid communication therebetween, and Heparin is injected into manifold 30 and through CVC access lumen 21 in an amount which is determined by protocol. Reagent syringe 38 is subsequently clamped off from manifold barrel 30. It may be necessary in some cases to provide a different concentration of Heparin than is pre-packaged in the system. If so, Heparin can be injected through membrane 54 rather than from reagent syringe 38. Alternatively, reagent syringe 38 could be connected to manifold barrel 30 by a luer-lock connecter so that it could be removed and replaced by a syringe containing the desired concentration of Heparin.

To remove CVC access system 20 from the CVC, forward end 34 of manifold barrel 30 and CVC tube 24 are clamped, and female and male luer-lock connectors 22 and 35 are disconnected. CVC female luer-lock connector 22 is then suitably capped, such as with a sterile Heparin lock (not shown) supplied with CVC access system 20. CVC access system 20 is disposed of in an appropriate manner. It is not intended to be reused.

Variations of the above methodical steps can of course be accommodated by variations in the physical configuration of CVC access system 20. For instance, the system can be modified as required to accommodate procedures requiring different concentrations of anticoagulant or larger amounts of saline. The system can also be used for intermittent administration of intravenous drip medications or blood products.

An identical CVC access system 20 can also be used to withdraw blood through a CVC access lumen as described below. Again, the system is provided in a pre-filled condition, ready for immediate connection to CVC access lumen 21. Flush syringe 36 is pre-filled with saline. Reagent syringe 38 is pre-filled with a blood anti-coagulant such as Heparin. Withdrawal syringe 40 initially contains a small volume of saline. The internal volume of manifold barrel 30 itself is initially pre-filled with saline. Flush syringe 36, reagent syringe 38, and withdrawal syringe 40 are initially clamped off from manifold barrel 30.

CVC access system 20 is first connected to CVC access lumen 21 as described above. To remove Heparin from CVC access lumen 21, collapsed withdrawal syringe 40 is unclamped from manifold barrel 30 to allow fluid communication therebetween. Withdrawal syringe 40 is then expanded to withdraw Heparin-containing blood rearward into manifold barrel 30, past injection syringes 36 and 38, and into withdrawal syringe 40. Withdrawal syringe 40 is subsequently clamped off from manifold barrel 30.

A needle of a transfer syringe or blood collection device (not shown) is then inserted through membrane 54 into transfer lumen 41. Blood is withdrawn through manifold 30 and CVC access lumen 21.

After the desired blood quantity has been obtained, flush syringe 36 is unclamped from manifold barrel 30 to allow fluid communication therebetween. Flush syringe 36 is compressed to inject saline into manifold 30 and CVC access lumen 21 until CVC access lumen 21 is cleared of blood. Flush syringe 36 is subsequently clamped off from manifold barrel 30.

Reagent syringe 38 is then unclamped from manifold barrel 30 to allow fluid communication therebetween, and Heparin is injected into manifold 30 and CVC access lumen 21 in a prescribed amount of about two to three milliliters by compressing reagent syringe 38. Reagent syringe 38 is subsequently clamped off from manifold barrel 30.

CVC access system 20 is removed from the CVC access lumen as described above and discarded. CVC female luer-lock connector 22 is suitably recapped with a new luer-lock cap supplied with the CVC system.

FIG. 3 shows a second embodiment of a CVC access system in accordance with the invention, generally designated by the reference numeral 70. CVC access system 70 is similar in many respects to access system 20 of FIG. 1. Similar components have therefore been labelled with the same reference numerals, except that the suffix "a" has been added to these reference numerals in FIG. 3.

CVC access system 70 thus includes a disposable manifold barrel 30a and a plurality of injection or withdrawal syringes provided integrally therewith. Manifold barrel 30a extends from a rearward end 32a to a forward end 34a. Forward end 34a is provided with a male luer-lock connector 35a for connection to female luer-lock connector 22a of CVC access lumen 21a. A cap 37a is provided over luer-lock connector 35a for removal when the system is used.

CVC system 70 includes a flush injection syringe 36a and a reagent injection syringe 38a. Each of these injection syringes is connected in fluid communication with manifold barrel 30a between its rearward and forward ends 32a and 34a. Injection syringes 36a and 38a perform the same functions as the corresponding syringes of FIG. 1. However, syringes 36a and 38a are bulb-shaped rather than having bellows-like folds. This illustrates the fact that many types of syringes might advantageously be used with a CVC access system in accordance with the invention. Conventional plunger-type syringes could also be used. Syringes 36a and 38a are pre-filled with appropriate fluids as described above.

Furthermore, tubing lengths 46a are shown extending from manifold barrel 30a at approximate forty-five degree angles, illustrating that many physical arrangements and configurations of manifold barrel 30a and its associated components are possible and may be desirable while still falling within the scope of the invention. For example, the various components attached to manifold barrel 30a in some cases may not be coplanar with manifold barrel 30a, but instead may be raised above the plane of manifold barrel 30a by a dihedral angle so as to avoid contact and associated loss of sterility with other objects such as the patient's bedclothing, skin, and the like.

CVC system 70 also includes a fluid or waste blood withdrawal syringe 40a and a fluid transfer lumen 41a connected in fluid communication with manifold barrel 30a. Fluid withdrawal syringe 40a is connected at manifold barrel rearward end 32a. It is preferably provided integrally with manifold barrel 30a.

Transfer lumen 41a is connected for fluid communication with manifold barrel 30a at a position similar to that described above with reference to FIG. 1. It comprises a short tube 52a which extends at approximately forty-five degrees from manifold barrel 30a. The transfer lumen includes fluid connection means for allowing fluid transfer to and from a fluid transfer syringe 74 when such a transfer syringe 74 is connected to the transfer lumen. Rather than a pierceable membrane, however, the connection means in access system 70 is formed by the termination of transfer lumen 41a in a mating connector 72. Mating connector 72 is preferably a female luer-lock connector which is initially capped with a male luer-lock cap 73. Mating connector 72 is connectable to collapsible transfer syringe 74 to allow fluid communication between the transfer syringe and manifold barrel 30a through transfer lumen 41a.

Transfer syringe 74 can take a variety of forms, including that of a conventional plunger syringe or blood collection device such as a Vacutainer blood withdrawal tube. Furthermore, transfer syringe 74 can be initially configured for either medication injection, intravenous push or drip, blood products administration, or blood sample withdrawal. FIG. 3 shows only one example of a transfer syringe. For example, another type of transfer syringe, particularly useful for blood withdrawal and collection, is described with reference to FIGS. 12 and 13 below.

In the embodiment of FIG. 3, transfer syringe 74 comprises a collapsible syringe tube 76. Syringe tube 76 has a closed rearward end 78. It has a male luer-lock connector 80 at its forward end. Syringe tube 76 has sidewalls in the form of accordion-like bellows or folds to allow axial expansion and compression of transfer syringe 74. Syringe tube 76 forms an internal volume which increases and descreases with the expansion and compression of transfer syringe 74.

Transfer syringe 74 is connectable to transfer lumen 41a to allow fluid transfer between transfer syringe 74 and manifold barrel 30a. Once connected, it is used in the same way as the needle-tipped transfer syringe described above with reference to FIG. 1. Transfer syringe 74 can be connected to manifold barrel 30a either before or after the CVC access system has been connected to a patient's CVC access lumen, utilizing a clamp 60 (FIG. 2) over transfer lumen 41a as necessary. In some cases, transfer syringe 74 can be provided by the manufacturer already attached to CVC access system 70: either pre-filled with a desired medication or collapsed for withdrawing blood. Operation of CVC access system 70 is identical to that of the similar system described with reference to FIG. 1, except for the manner of connecting transfer syringe 74, as described above.

An additional advantage of CVC access system 70 is that transfer syringe 76 can be detached after blood withdrawal and used for subsequent blood processing. Transfer syringe 76 can be fabricated in a size and shape which allows it to be placed directly into a blood centrifuge, thus eliminating the previously-necessary step of transferring blood to a separate processing tube.

FIG. 4 shows a third embodiment of a CVC access system in accordance with the invention, generally designated by the reference number 90. CVC access system 90 is in many respects similar to access system 20 of FIG. 1. Similar components have therefore been labelled with the same reference numerals, except that the suffix "b" has been added to common reference numerals in FIG. 4.

CVC access system 90 includes a disposable manifold barrel 30b and a plurality of injection or withdrawal syringes provided integrally with manifold barrel 30b. Manifold barrel 30b extends from a rearward end 32b to a forward end 34b. Forward end 34b of manifold barrel 30b is provided with a male luer-lock connector 35b and is thus connectable to female luer-lock connector 22b of CVC access lumen 21b. A cap 37b is provided over luer-lock connector 35b for removal before system use.

CVC system 90 includes a fluid or waste blood withdrawal syringe 40b and a fluid transfer lumen 41b connected in fluid communication with manifold barrel 30b. fluid withdrawal syringe 40b is connected at the manifold barrel rearward end 32b. It is preferably provided integrally with manifold barrel 30b.

Transfer lumen 41b is connected for fluid communication with manifold barrel 30b at a position similar to that described above with reference to FIG. 1. It comprises a short tube 52b which extends from manifold barrel 30b. The transfer lumen includes fluid connection means for allowing fluid transfer to and from a transfer syringe. The connection means in access system 90 is formed by a direct connection between transfer lumen 41b and an integral transfer syringe 92. Transfer syringe 92 is initially supplied either in a compressed or expanded condition, depending upon whether the CVC access system is intended to be used for blood collection or for medication injection. If CVC access system 90 will be used to withdraw blood, transfer syringe 92 is initially collapsed. If CVC access system 90 will be used to inject medication, transfer syringe 92 is initially expanded and prefilled with the medication.

Structurally, transfer syringe 92 comprises a syringe tube having accordion-like bellows or folds to allow axial compression and expansion. It is connected directly to transfer lumen 41b to allow fluid communication therebetween, and selectively clamped off as necessary to prevent intermingling between fluids contained in transfer syringe 92 and fluids within manifold barrel 30b. Transfer syringe 92 is used in the same way as the needle-tipped transfer syringe described above with reference to FIG. 1.

In place of dual injection syringes 36 and 38, as shown in FIG. 1, CVC access system 90 includes a single, multi-phase injection syringe 94 having at least two internal fluid cells. Multi-phase injection syringe 94 functions as both a flush syringe and a reagent syringe. It is connected in fluid communication with manifold barrel 30b rearward of transfer lumen 41b, being operable to sequentially inject fluid from its two internal fluid cells into manifold barrel 30b.

More specifically, and referring also to FIG. 5, multi-phase injection syringe 94 comprises a collapsible hollow body or syringe tube 100 which extends axially from a rearward end 102 to a forward end 104. Syringe tube 100 has sidewalls 106 in the form of accordionlike bellows to allow axial compression of syringe tube 100. Syringe tube rearward end 102 is closed. Syringe tube 100 has a hollow interior enclosing a fluid volume which decreases with axial compression of syringe tube 100.

At least one generally transverse breachable septum 110 is positioned within syringe tube 100 between its forward and rearward ends 104 and 102. Septum 110 is impermeable while also being thin enough to be easily breached by piercing, rupturing, or puncturing. Septum 110 is axially positioned to divide the syringe tube hollow interior into at least forward and rearward fluid cells 112 and 114. A syringe tip 108 is formed in forward end 104 of syringe tube 100 adjacent forward cell 112 of the syringe tube hollow interior. Syringe tip 108 has an opening or passage 109 through which fluid passes from the syringe tube forward fluid cell into manifold barrel 30b upon axial compression of syringe tube 100.

Each fluid cell 112 and 114 is typically pre-filled with a liquid for sequential injection through syringe tip 108. Syringe tube forward cell 112 is typically pre-filled with a flush fluid such as normal saline solution. Rearward cell 114 is pre-filled with a reagent fluid or a blood anti-coagulant such as Heparin. A puncture member 115 is positioned within syringe tube 100 to puncture septum 110 after forward cell 112 has been at least partially emptied by partial axial compression of syringe tube 100. Puncturing septum 110 allows fluid passage from rearward cell 114 through opening 109 of syringe tip 108, resulting in sequential injection of saline and blood anti-coagulant into manifold barrel 30b. Puncture member 115 is positioned at forward end 104 of syringe tube 100, adjacent syringe tip 108, to contact septum 110 only after syringe tube 100 has been sufficiently compressed to substantially empty forward cell 112. FIG. 6 shows syringe tube 100 as septum 110 is punctured by axial compression of syringe tube 100.

Syringe tube 100, including syringe tip 108, septum 110, and puncture member 115, is preferably integrally molded or formed from flexible plastic or plastic-like materials such as a number of well-known polymers or other medically-approved materials. High density polyethylene is an example of a suitable material. Certain types of ceramics could also be used. Puncture member 115 is formed in any suitable shape which will puncture septum 110.

Operation of CVC access system 90 for medication injection proceeds in a manner quite similar to that described above with reference to FIG. 1. However, injecting Heparin requires first exhausting the flush fluid within multi-phase syringe 94, and puncturing septum 110 by further compression of syringe tube 100.

When used to dispense medication, transfer syringe 92 may be pre-filled with the desired medication, depending on dosage considerations.

CVC access system 90, with integral transfer syringe 92, can also be used for CVC blood sample collection by providing transfer syringe 92 in a collapsed form. However, a manner of detaching transfer syringe 92 must be made available. One such manner of detachment has already been described with reference to FIG. 3. The blood collection steps described below assume that a manner of detachment has been provided.

In specific operation, CVC access system 90 is connected to CVC access lumen 21b in a manner identical to that described above with reference to FIG. 1. Withdrawal of waste or Heparin-containing blood also proceeds, if necessary, as already described with reference to FIG. 1.

When using CVC access system 90 to inject medication, multi-phase injection syringe 94 is unclamped from manifold barrel 30b to allow fluid communication therebetween. Multi-phase injection syringe 94 is partially compressed to inject a first prescribed amount of saline into manifold 30b from forward fluid cell 112. Multi-phase injection syringe 94 is subsequently clamped off from manifold barrel 30b. Transfer syringe 92 is then unclamped from manifold barrel 30b and compressed to inject medication into manifold 30b through transfer lumen 41b. Transfer syringe 92 is subsequently clamped off. Multi-phase injection syringe 94 is again unclamped from manifold barrel 30b to allow fluid communication therebetween, and compressed to inject an additional amount of saline into manifold 30b and through CVC access lumen 21b into the patient. Multi-phase injection syringe 94 is further compressed to puncture septum 110 and to finally inject anti-coagulant into manifold 30b and through CVC access lumen 21b. Multi-phase injection syringe 94 is subsequently clamped off from manifold barrel 30b. CVC access system 90 is then removed and discarded.

When using CVC access system 90 to withdraw blood, transfer syringe 92 is unclamped from manifold barrel 30b, after withdrawal of Heparin-containing blood, to allow fluid communication between transfer syringe 92 and manifold barrel 30b. Transfer syringe 92 is expanded to withdraw the requisite amount of blood and then clamped off. Multi-phase injection syringe 94 is unclamped from manifold barrel 30b to allow fluid communication therebetween. Multi-phase injection syringe 94 is partially compressed to inject saline into manifold 30b from forward fluid cell 112. Multi-phase injection syringe 94 is then further compressed to puncture septum 110 and to inject Heparin into manifold 30b and through CVC access lumen 21b.

Multi-phase injection syringe 94 can be used independently of CVC access system 90, for providing direct medication injection. For example, syringe tube 100 can be provided with a syringe needle and used for hypodermic injections of multiple sequential medications. Alternatively, syringe tip 108 can be provided with a male luer-lock connector for direct connection to either a needle, a CVC access lumen, or to a CVC access system transfer lumen such as 41a shown in FIG. 3. The multi-phase capability of injection syringe 94 allows convenient injection of more than one medication even when such medications cannot be mixed. As an example, multi-phase injection syringe 94 is particularly appropriate for medications used during emergency-room or other "code" situations, in which a fixed dosage is uniformly administered to all patients, regardless of weight or other variables. Lidocaine, epinephrine, glucose solutions, and bicarbonate solutions are examples of such medications.

Furthermore, an alternative embodiment of the multiphase injection syringe, generally designated by the reference numeral 120 in FIG. 7, can be used for sequential injection of more than two solutions or medications. Multi-phase injection syringe 120 is similar in many details to syringe 94 of FIGS. 4–6. Accordingly, like features have been designated with like reference numerals, with the addition of the suffix "a" to common reference numerals in FIG. 7. Multi-phase injection syringe 120 thus comprises a collapsible hollow body or syringe tube 100a which extends axially from a rearward end 102a to a forward end 104a. Syringe tube 100a has sidewalls 106a in the form of accordion-like bellows to allow axial compression of syringe tube 100a. Rearward end 102a is closed. Syringe tube 100a has a hollow interior enclosing a fluid volume which decreases with axial compression of syringe tube 100a.

Syringe tube 100a includes multiple septums dividing the syringe tube hollow interior into multiple fluid cells. More specifically, a forward septum 122 and a rearward septum 124 divide the syringe tube hollow interior into a forward fluid cell 126, an intermediate fluid cell 127, and a rearward fluid cell 128. Furthermore, multi-phase injection syringe 120 includes multiple puncture members within the syringe tube hollow interior to sequentially puncture multiple septums 122 and 124, and to allow sequential injection of fluid from the multiple fluid cells. A forward puncture member 130 is similar in position and shape to puncture member 115 of FIGS. 4–6. A rearward puncture member 132 is positioned on the rearward surface of forward septum 122 to contact and pierce rearward septum 124 upon collapse of intermediate fluid cell 127. Alternatively, a single puncture member, positioned at the forward end of syringe tube 100a, could be used to puncture each septum at that septum reaches the forward end of syringe tube 100a. Injection syringe 120, including its septums and puncture members, is preferably integrally molded or formed from a number of well-known polymers or other medically-approved materials, such as high density polyethylene. Certain types of ceramics could also be used. The fluid cells of injection syringe 120 are pre-filled with appropriate solutions or medications.

Figure 9:
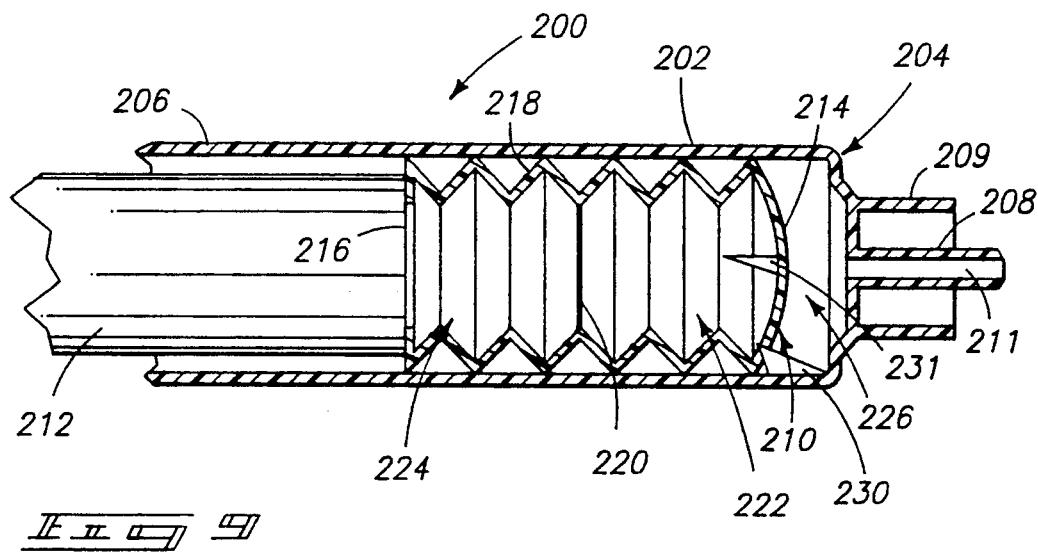
FIG. 9 is a sectional front view of the multi-phase injection syringe of FIG. 8, the syringe being shown in a partially compressed condition.
Figure 10:
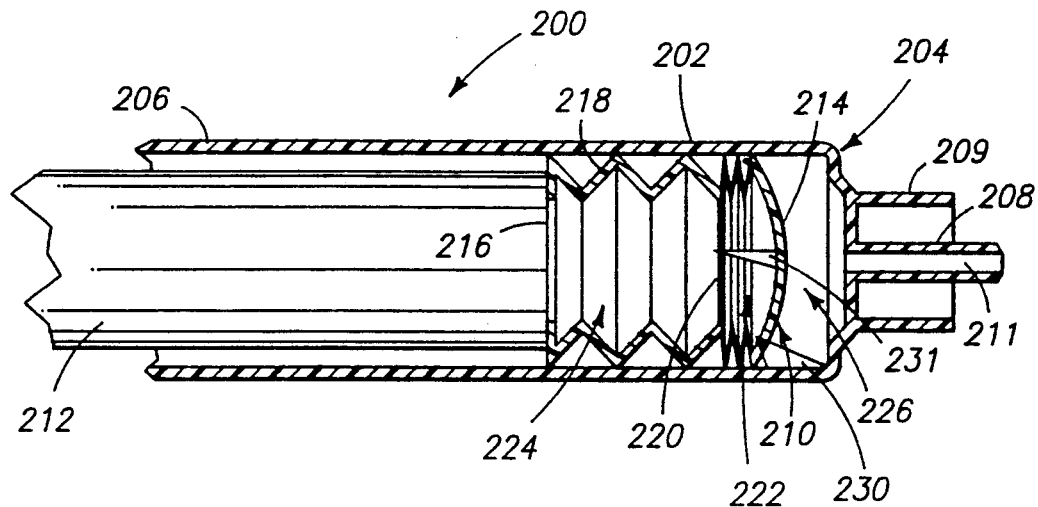
FIG. 10 is a sectional front view of the multi-phase injection syringe of FIG. 8, the syringe being shown in a further compressed condition.

FIGS. 8–10 show yet another embodiment of a multiphase injection syringe in accordance with the invention, generally designated by the reference numeral 200. Injection syringe 200 includes a rigid cylindrical syringe tube 202 having forward and rearward ends 204 and 206, respectively. Syringe tube 202 is open at its rearward end 206. A syringe tip 208 is positioned at syringe tube forward end 204. Syringe tip 208 has an opening or passage 211 to allow fluid passage from the syringe tube. Syringe tip 208 is typically provided with an integral male luer-lock connector 209.

A collapsible hollow body 210 is slidably received within syringe tube 202, essentially replacing the rubber plunger of a conventional plunger-type syringe. An elongated rod or actuator handle 212 extends rearwardly from hollow body 210, and extends out through rearward end 206 for grasping by an operator.

Hollow body 210 has closed forward and rearward ends 214 and 216, and sidewalls 218 which extend axially within rigid tube 202. Sidewalls 218 are in the form of accordion-like bellows or folds to allow axial compression and expansion of hollow body 210. A thin but impermeable septum 220 within the hollow body divides the interior of the hollow body into forward and rearward fluid cells 222 and 224, respectively, which are pre-filled with desired solutions or medications.

The bellows-like folds of hollow body 210 form an outer periphery having a diameter sufficient to insure a sliding friction fit and seal between hollow body 210 and rigid syringe tube 202, thus providing a sealed interior volume 226 within rigid tube 202 forward of hollow body 210. Fluid passes from sealed interior volume 226 through opening 211 of syringe tip 208. A forward puncture member 230 is positioned within syringe tube 202 at its forward end 204 adjacent syringe tip 208 to puncture closed forward end 214 of hollow body 210 upon sufficient forward movement of actuator handle 212, after the fluid content of interior volume 226 has been substantially exhausted. Puncturing or otherwise breaching forward end 214 allows fluid passage from forward cell 222 through syringe tube opening 211. A rearward puncture member 231 is positioned within hollow body 210, projecting rearwardly from forward end 214, to puncture septum 220 after forward cell 222 has been emptied or at least partially emptied by compression or partial compression of hollow body 210. Puncturing or otherwise breaching septum 220 allows fluid passage from rearward cell 224 of hollow body 210 through opening 211 of syringe tip 208.

Operation of multi-phase injection syringe 200 is best explained with reference to FIGS. 9 and 10. The fluid cells of hollow collapsible body 210 are pre-filled with appropriate fluids. Sealed interior volume 226 can be pre-filled or filled with an appropriate fluid in a conventional manner just prior to use. Initially, an operator presses actuator handle 212 to inject fluid from sealed interior volume 226. When interior volume 226 has been substantially emptied, forward puncture member 230 contacts and pierces forward end 214 of hollow body 210 (FIG. 9), allowing fluid from forward fluid cell 222 to flow out of syringe tube 202 through opening 211 of syringe tip 208. The operator continues to press handle 212 to compress the forward portion of hollow body 210, until eventually most of the fluid has been exhausted from forward fluid cell 222. Once this has happened, rearward puncture member 231 is in close proximity to septum 220 (FIG. 10). Further compression of hollow body 210 punctures septum 220, allowing fluid from rearward fluid cell 224 to be injected from injection syringe 200 through opening 211 of syringe tip 208.

FIG. 11 shows yet another embodiment of a multiphase injection syringe in accordance with the invention, generally designated by the reference numeral 230. Injection syringe 230 is in many respects similar to multi-phase injection syringe 200 shown in FIGS. 8–10. Accordingly, similar features have been designated with like reference numerals, with the addition of the suffix "a" in FIG. 11. Injection syringe 230 includes a rigid cylindrical syringe tube 202a having forward and rearward ends 204a and 206a, respectively. Syringe tube 202a is open at its rearward end 206a. A syringe tip 208a is positioned at syringe tube forward end 204a, having an opening or passage 211a to allow fluid passage from the syringe tube. Syringe tip 208a is also provided with an integral male luer-lock connector 209a.

A collapsible hollow body 210a is slidably received within syringe tube 202a. An elongated rod or actuator handle 212a extends rearwardly from hollow body 210a. Hollow body 210a has closed forward and rearward ends 214a and 216a, and sidewalls 218a which extend axially within rigid tube 202a. Sidewalls 218a are in the form of accordion-like bellows or folds to allow axial compression and expansion of hollow body 210a.

The bellows-like folds of hollow body 210a form an outer periphery having a diameter sufficient to insure a sliding friction fit and seal between hollow body 210a and rigid syringe tube 202a, thus providing a sealed interior volume 226a within rigid tube 202a forward of hollow body 210a.

Multiple septums are formed within hollow body 210a. Specifically, a forward septum 252 and a rearward septum 254 divide the hollow interior of hollow body 210a into three fluid cells: a forward fluid cell 256, an intermediate fluid cell 258, and a rearward fluid cell 260.

A forward puncture member 230a is positioned within syringe tube 202a at its forward end 204a adjacent syringe tip 208a to breach or puncture closed forward end 214a of hollow body 210a upon sufficient forward movement of actuator handle 212a, when the fluid content of interior volume 226a has been substantially exhausted. An intermediate puncture member 262 is positioned within hollow body 210a, projecting rearwardly from forward end 214a, to breach or puncture forward septum 252 after forward cell 256 has been emptied or at least partially emptied by compression or partial compression of hollow body 210a. Puncturing septum 252 allows fluid passage from intermediate cell 258 of hollow body 210a through opening 211a of syringe tip 208a.

A rearward puncture member 264 is also positioned within hollow body 210a, projecting rearwardly from forward septum 252, to breach or puncture rearward septum 254 after intermediate cell 258 has been emptied or at least partially emptied by compression or partial compression of hollow body 210a. Rearward puncture member 264 is cylindrically shaped to accommodate intermediate puncture member 262. Puncturing rearward septum 254 allows fluid passage from rearward fluid cell 260 of hollow body 210a through opening 211a of syringe tip 208a.

The fluid cells of multi-phase injection syringe 230 are pre-filled with appropriate amounts and types of fluids. Sealed internal volume 226a can be either pre-filled or filled just prior to use.

The hollow bodies 210 and 210a, including their associated septums and puncture members as described with reference to FIGS. 8-11, are integrally formed or molded of a flexible plastic or plastic-like material such as a number of well-known polymers or ceramics, including high density polyethylene.

FIGS. 12 and 13 show a preferred blood collection device 300 for use with the CVC access systems described above and for other uses. Blood collection device 300 is designed for connection to a transfer lumen such as transfer lumen 41a, described above with reference to FIG. 3.

Specifically, blood collection device 300 comprises a rigid cylindrical syringe tube 302 extending from a rearward end 304 to a forward end 306. The rigid tube is open at its rearward end 304. Rigid tube 302 has a hollow interior formed along its length. A syringe tip 308 is formed in syringe tube forward end 306. Syringe tip 308 is typically provided with an integral male luer-lock connector 309. Such a connector is advantageously used for connection to an intravenous needle or to a central venous catheter system such as described above.

Blood collection device 300 also includes a rubber or rubber-like piston or plunger 320 which is slidably received within the hollow interior of syringe tube 302. The plunger is similar to a conventional syringe plunger, except that it is not attached to a conventional actuator rod or handle. It is formed in the shape of a disk, with an outer periphery complementary to the inner periphery of syringe tube 302 to slidingly seal against syringe tube 302. Plunger 320 defines a variable blood collection volume 321 in forward end 306 of syringe tube 302. An opening or passage 311 is formed in syringe tip 308 to allow fluid passage into blood collection volume 321.

Rather than a conventional plunger actuator handle, which would normally extend longitudinally rearward from plunger 320 to allow an operator to move plunger 320 in both forward and rearward directions, collection device 300 includes a flexible tension line 322. Tension line 322 comprises a flexible ligament, string, cord, or chain which is connected to the rear of plunger 320 and which extends rearwardly out of syringe tube 302 through its rearward end 304. An operator grip 330 is attached to tension line 322 at its rearward end. Tension line 322 is operable to pull plunger 320 toward rearward end 304 of syringe tube 302 to increase the blood collection volume and to draw blood into syringe tube 302 through syringe tip 308. However, tension line 322 is flexible so that it is inoperable to push plunger 320 back toward forward end 306 of syringe tube 302. A plunger stop is formed in syringe tube 302 at its rearward end 304 in the form of a shoulder 332 to limit rearward movement of plunger 320 and to prevent an operator from pulling plunger 320 completely out of syringe tube 302. Shoulder 332 extends completely about the cylindrical inner periphery of syringe tube 302.

Tension line 322 is preferably a flexible thread or filament which is capable of transmitting force to plunger 320 in a rearward direction, but is incapable of transmitting force in a forward direction. As shown in FIG. 13, pushing tension line 322 forward results in the line laying limp within or behind syringe tube 302. Because of this feature, one-way operation of plunger 320 is assured. One-way operation is a desirable feature in a blood collection device because blood collection tubes are often pre-filled with reagents which would be harmful if accidently injected into a patient's bloodstream. Furthermore, the device described above is advantageous over prior art devices such as Vacutainer blood withdrawal tubes because an operator is able to "feel" the response of the device to applied rearward forces, and to gently adjust those forces as necessary for optimum results. This is in contrast to the predetermined vacuum which is abruptly applied by a Vacutainer blood withdrawal tube.

Blood collection device 300 has further advantages in that its unique physical configuration allows it to be conveniently used in a conventional centrifuge chamber, eliminating the need for transferring the withdrawn blood into a separate processing tube. Standard centrifuge chambers are typically formed by a cylindrical sleeve having a generally planar support surface. The cylindrical sleeve is normally of a standard diameter. Syringe tube 302 has an outer diameter which is compatible with such centrifuge chamber sleeves, allowing blood collection device 300 to be received therein. Furthermore, when used for this purpose tension line 322 can be conveniently snipped off or simply stuffed within the rearward end of syringe tube 302. This allows rearward end 304 of syringe tube 302 to be used as a support base. The support base formed by rearward end 304 is sized and shaped to bear against the planar support surface of a centrifugal processing chamber, and to support blood collection device 300 during centrifugal processing. Plunger 320 is supported, in turn, by shoulder 332 during such processing.

To further facilitate centrifugal processing, syringe tube 302 can be fabricated with a forward end 306 which is removable or detachable to allow access to the interior of syringe tube 302. Where such a removable end is provided, it is also desirable to provide an end cap for capping forward end 306 after blood withdrawal or processing to preserve the quality of the blood specimen. In addition, syringe tube 302 is advantageously formed of a clear or nearly clear material to allow its contents to easily be viewed after processing.

The CVC access system described above provides an integrated solution to the problems associated with CVC access operations. One integral package provides all required CVC access functions such as waste blood withdrawal, flush and reagent injection, medication injection (including intravenous push or drip and blood product administration), and blood collection. The use of a pierceable membrane over the CVC access-lumen can be eliminated. In some cases, the use of pierceable membranes is completely eliminated. The questionable sterility and integrity of such pierceable membranes is thus eliminated from consideration.

With the CVC access systems described above, only one hook-up to a CVC access-lumen is required, rather than the minimum of four hook-ups previously required. The elimination of needles in the procedure greatly reduces the chance that the care giver will be injured or infected during the process. Avoiding air embolism is accomplished by pre-filling the access system with sterile saline solution.

All needed parts of the access system are packaged and sealed together. Accordingly, the potential for introduction of contamination while hooking-up the parts is virtually eliminated. Similarly, time wasted in searching, cleaning, and connecting non-compatible parts is eliminated. When packaged for blood withdrawal, the system includes a blood collection device such as described above with reference to FIGS. 12 and 13. This blood collection device provides the convenience of "Vaculainer blood withdrawal tubes" without the disadvantages associated with drawing blood through application of an unpredictable source of vacuum. The system allows a systematic approach which greatly reduces the time required to perform CVC access functions.

In compliance with the statute, the invention has been described in language more or less specific as to structural and methodical features. It is to be understood, however, that the invention is not limited to the specific features described, since the means herein disclosed comprise preferred forms of putting the invention into effect. The invention is, therefore, claimed in any of its forms or modifications within the proper scope of the appended claims appropriately interpreted in accordance with the doctrine of equivalents.

I claim:

1. A central venous catheter access apparatus, comprising:

a central venous access system comprising a manifold;

central venous catheter connector means for connecting the access system to a central venous catheter, the central venous catheter connector means being in bi-directional fluid communication with the manifold for providing bi-directional fluid communication between the manifold and a central venous catheter when the access system is connected to a central venous catheter;

a flush syringe connected in fluid communication with the manifold, the manifold and central venous catheter connector means providing fluid communication from the flush syringe to a central venous catheter when the access system is connected to a central venous catheter;

a fluid withdrawal syringe connected in fluid communication with the manifold, the manifold and central venous catheter connector means providing fluid communication between a central venous catheter and the fluid withdrawal syringe to allow withdrawal of fluid from a central venous catheter through the connector means when the access system is connected to a central venous catheter; and a transfer lumen connected in fluid communication with the manifold, the manifold and central venous catheter connector means providing fluid communication between the transfer lumen and a central venous catheter when the access system is connected to a central venous catheter, the transfer lumen allowing fluid passage between a transfer syringe and a central venous catheter when the access system is connected to a central venous catheter.

2. A central venous catheter access system as recited in claim 1 wherein the access system forms an internal system volume which is pre-filled with a liquid to substantially eliminate air from the internal system volume.

3. A central venous catheter access system as recited in claim 1 and further comprising a reagent syringe connected in fluid communication with the manifold, the manifold and central venous catheter connector means providing fluid communication from the reagent syringe to a central venous catheter when the access system is connected to a central venous catheter.

4. A central venous catheter access system as recited in claim 1 and further comprising a pierceable membrane positioned relative to the transfer lumen to allow a transfer syringe needle to be inserted into the transfer lumen.

5. A central venous catheter access system as recited in claim 1 wherein the transfer lumen terminates in a mating connector, the mating connector being connectable to a transfer syringe to allow fluid communication between a transfer syringe and the manifold through the transfer lumen.

6. A central venous catheter access system as recited in claim 1 and further comprising a transfer syringe connected for fluid communication with the transfer lumen to transfer fluid between the transfer syringe and a central venous catheter when the access system is connected to a central venous catheter to allow withdrawal of a blood sample from a patient through said central venous catheter.

7. A central venous catheter access system as recited in claim 1 wherein the flush syringe comprises a multiphase injection syringe, the multi-phase injection syringe having at least two fluid cells and being operable to sequentially inject fluid from said two fluid cells into the manifold.

8. A central venous catheter access apparatus, comprising:
a central venous catheter access system comprising a manifold;
central venous catheter connector means for connecting the access system to a central venous catheter, the central venous catheter connector means being in bi-directional fluid communication with the manifold for providing bi-directional fluid communication between the manifold and a central venous catheter when the access system is connected to a central venous catheter;
a flush syringe connected in fluid communication with the manifold, the manifold and central venous catheter connector means providing fluid communication from the flush syringe to a central venous catheter when the access system is connected to a central venous catheter;
a fluid withdrawal syringe connected in fluid communication with the manifold, the manifold and central venous catheter connector means providing fluid communication between a central venous catheter and the fluid withdrawal syringe to allow withdrawal of fluid from a central venous catheter through the connector when the access system is connected to a central venous catheter;
a transfer lumen connected in bi-directional fluid communication with the manifold, the manifold and central venous catheter connector means providing bi-directional fluid communication between the transfer lumen and a central venous catheter when the access system is connected to a central venous catheter, the transfer lumen allowing withdrawal of a blood sample from a patient through a central venous catheter when the access system is connected to a central venous catheter; and
the central venous catheter access system forming an internal system volume which is pre-filled with a liquid to substantially eliminate air from the internal system volume.

9. A central venous catheter access system as recited in claim 8 and further comprising a reagent syringe connected in fluid communication with the manifold, the manifold and central venous catheter connector means providing fluid communication from the reagent syringe to a central venous catheter when the access system is connected to a central venous catheter.

10. A central venous catheter access system as recited in claim 8 and further comprising a reagent syringe connected in fluid communication with the manifold, the manifold and central venous catheter connector means providing fluid communication from the reagent syringe to a central venous catheter when the access system is connected to a central venous catheter, the reagent syringe being pre-filled with a blood anti-coagulant for selective injection into the manifold.

11. A central venous catheter access system as recited in claim 8 wherein the flush syringe comprises a multi-phase injection syringe, the multi-phase injection syringe having at least forward and rearward fluid cells, the forward fluid cell containing a flush fluid, the rearward fluid cell containing a reagent fluid, the multi-phase injection syringe being operable to sequentially inject the flush fluid and the reagent fluid into the manifold barrel.

12. A central venous catheter access system as recited in claim 8 and further comprising a pierceable membrane positioned relative to the transfer lumen to allow a transfer syringe needle to be inserted into the transfer lumen.

13. A central venous catheter access system as recited in claim 8 wherein the transfer lumen terminates in a mating connector, the mating connector being connectable to a transfer syringe to allow fluid communication between a transfer syringe and a central venous catheter when the access system is connected to a central venous catheter.

14. A central venous catheter access system as recited in claim 8 and further comprising a transfer syringe connected for fluid communication with the transfer lumen to transfer fluid between the transfer syringe and a central venous catheter when the access system is connected to a central venous catheter.

15. A central venous catheter access apparatus, comprising:
a central venous catheter access system comprising a manifold;
central venous catheter connector means for connecting the access system to a central venous catheter, the central venous catheter connector being in bi-directional fluid communication with the manifold for providing bi-directional fluid communication between the manifold and a central venous catheter when the access system is connected to a central venous catheter;
a fluid withdrawal syringe connected in fluid communication with the manifold, the manifold and central venous catheter connector means providing fluid communication between a central venous catheter and the fluid withdrawal syringe to allow withdrawal of fluid from a central venous catheter through the connector when the access system is connected to a central venous catheter;
a flush syringe connected in fluid communication with the manifold, the manifold and central venous catheter connector means providing fluid communication from the flush syringe to a central venous catheter when the access system is connected to a central venous catheter, the flush syringe being pre-filled with a flush fluid for selective injection into the manifold and into a central venous catheter;
a reagent syringe connected in fluid communication with the manifold, the manifold and central venous catheter connector providing fluid communication from the reagent syringe to a central venous catheter when the access system is connected to a central venous catheter, the reagent syringe being pre-filled with a blood anti-coagulant for selective injection into the manifold;
a transfer lumen connected in bi-directional fluid communication with the manifold for connection to a transfer syringe, the manifold and central venous catheter connector providing bi-directional fluid communication between the transfer lumen and a central venous catheter when the access system is connected to a central venous catheter, the transfer lumen allowing withdrawal of a blood sample from a patient through a central venous catheter when a transfer syringe is connected to the transfer lumen;
the central venous catheter access system forming an internal system volume which is pre-filled with a liquid to substantially eliminate air from the internal system volume.

16. A central venous catheter access system as recited in claim 15 and further comprising a pierceable membrane positioned relative to the transfer lumen to allow a transfer syringe needle to be inserted into the transfer lumen.

17. A central venous catheter access system as recited in claim 15 wherein the transfer lumen terminates in a mating connector, the mating connector being connectable to a transfer syringe to allow fluid communication between a transfer syringe and a central venous catheter through the transfer lumen when the access system is connected to a central venous catheter.

18. A central venous catheter access system as recited in claim 15 and further comprising a transfer syringe connected for fluid communication with the transfer lumen to transfer fluid between the transfer syringe and a central venous catheter when the access system is connected to a central venous catheter.

* * * * *